(12) United States Patent
Essner et al.

(10) Patent No.: US 7,653,427 B2
(45) Date of Patent: Jan. 26, 2010

(54) METHOD AND INSTRUMENT FOR MINIMALLY INVASIVE SENTINEL LYMPH NODE LOCATION AND BIOPSY

(75) Inventors: Richard Essner, Santa Monica, CA (US); Farhad Daghighian, Santa Monica, CA (US); Henry Daghighian, Mountain View, CA (US)

(73) Assignee: Intra-Medical Imaging LLC, Los Angeles, CA (US)

( * ) Notice: Subject to any disclaimer, the term of this patent is extended or adjusted under 35 U.S.C. 154(b) by 295 days.

(21) Appl. No.: 11/270,906

(22) Filed: Nov. 10, 2005

(65) Prior Publication Data

US 2006/0106306 A1  May 18, 2006

Related U.S. Application Data

(60) Provisional application No. 60/656,565, filed on Feb. 25, 2005, provisional application No. 60/633,122, filed on Dec. 3, 2004, provisional application No. 60/627,365, filed on Nov. 12, 2004.

(51) Int. Cl.
    *A61B 6/00* (2006.01)
(52) U.S. Cl. .................. 600/436; 600/437; 600/427; 600/478; 600/473; 607/96; 250/336
(58) Field of Classification Search ................. None
    See application file for complete search history.

(56) References Cited

U.S. PATENT DOCUMENTS

| | | | | |
|---|---|---|---|---|
| 4,029,964 A | * | 6/1977 | Ashe | 250/368 |
| 5,805,664 A | * | 9/1998 | Whipple et al. | 378/117 |
| 5,846,513 A | * | 12/1998 | Carroll et al. | 424/1.11 |
| 5,865,744 A | * | 2/1999 | Lemelson | 600/407 |
| 5,961,458 A | * | 10/1999 | Carroll | 600/436 |
| 6,037,129 A | * | 3/2000 | Cole et al. | 435/6 |
| 6,464,625 B2 | * | 10/2002 | Ganz | 600/3 |
| 6,512,943 B1 | | 1/2003 | Kelcz | |
| 6,638,234 B2 | * | 10/2003 | Burbank et al. | 600/564 |
| 6,804,549 B2 | * | 10/2004 | Hayashi | 600/431 |
| 6,946,841 B2 | | 9/2005 | Rubashov | |

\* cited by examiner

*Primary Examiner*—Long V Le
*Assistant Examiner*—Joel F Brutus
(74) *Attorney, Agent, or Firm*—Koppel, Patrick, Heybl & Dawson; Michael J. Ram

(57) ABSTRACT

The present invention is directed to instruments and instrumental techniques for locating cancer cells in lymph nodes which utilize a radiation detector operatively connected to an ultrasound probe for locating the exact position of radiation tagged tissue, particularly in sentinel lymph nodes followed by placement of a biopsy device. Also described are unique new interoperative radiation detection probes for use in these techniques which include structure for placement of a biopsy device or biopsy needle into the located lymph node and procedures for removal of small portions of detected radiation emitting sentinel lymph nodes for evaluation in a pathology laboratory by measurement of expressed genes located in the removed tissue. The instruments and instrumental techniques also facilitate the subsequent delivery of materials to reverse the unfavorable immune response or environment conducive for metastasis in the sentinel lymph node once cancer cells are located therein.

21 Claims, 13 Drawing Sheets

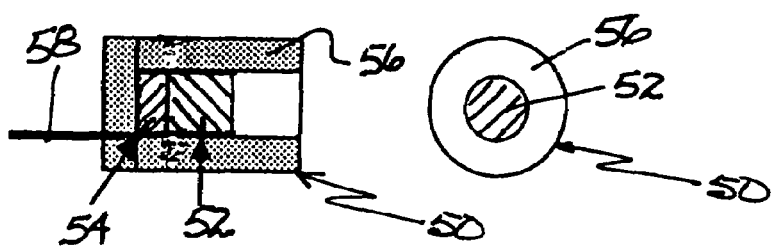
FIGURE 20a     FIGURE 20b
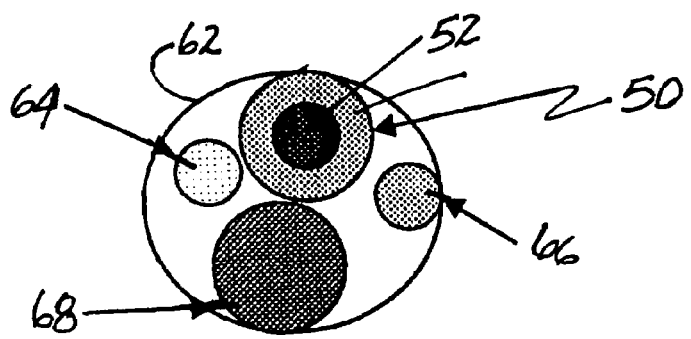
FIGURE 21
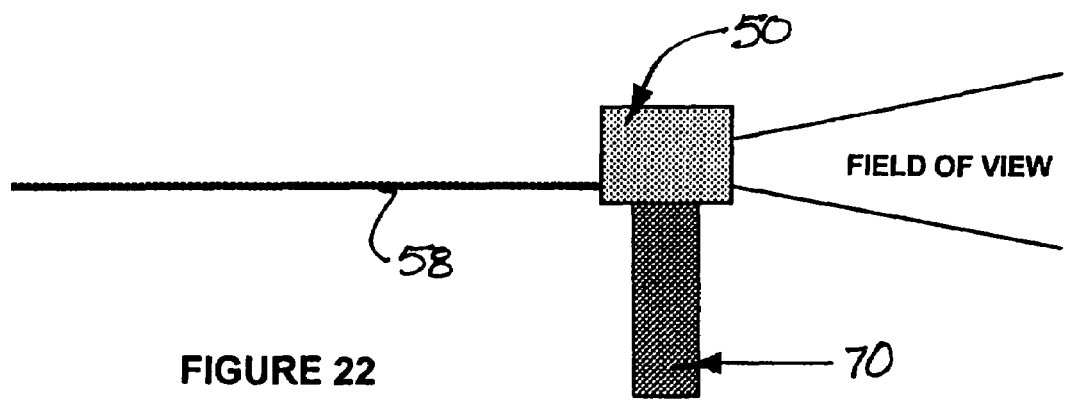
FIGURE 22

METHOD AND INSTRUMENT FOR MINIMALLY INVASIVE SENTINEL LYMPH NODE LOCATION AND BIOPSY

This application claims benefit of Provisional Application Ser. No. 60/627,365 filed Nov. 12, 2004, Provisional Application Ser. No. 60/633,122 filed Dec. 3, 2004 and Provisional Application Ser. No. 60/656,565 filed Feb. 25, 2005.

The present invention is directed to instrumental techniques for locating cancer cells in sentinel nodes, interoperative radiation detection probes for use in these techniques and the procedures for surgical removal of small portions of detected radiation emitting sentinel lymph nodes for evaluation in a pathology laboratory.

BACKGROUND

The presence of cancer cells in sentinel lymph nodes is an indication that a cancer has metastasized. Pathological evaluation of these lymph nodes is presently used for staging of melanoma and breast cancers. The sentinel lymph node must first be detected and distinguished from other lymph nodes. This is accomplished by use of radiotracers and blue dye. Radioactive tracer (such as Tc-99m sulfur colloid) is injected around the tumor. This tracer then migrates to the lymph nodes. Utilizing a gamma camera, the sentinel lymph node which now contains the radioactive tracer is located. The patient is then moved to the operating room, where the surgeon injects blue dye around the tumor, and makes an incision in the region marked as being over the area of the sentinel lymph node. The surgeon locates the sentinel node using a gamma ray detecting probe. The sentinel node is then further identified and distinguished from other nodes by visual inspection as to which of the lymph node contains the blue dye that was injected around the tumor. The whole lymph node is then resected and sent to the pathology lab for analysis. In the laboratory, several slices of the removed node are prepared and examined under a microscope to determine if any cancer cells are in that sentinel lymph node.

One of the negative aspects of this procedure is that the whole lymph node must be removed for pathological examination, which requires a surgical incision. The pathologist must then prepare numerous slices of the lymph node and examine each slice, in order to determine if the sentinel node is completely free of cancer cells (tumor-negative.) Even one cancer cell would render the sentinel node tumor-positive and would put the patient into stage 3, requiring the surgeon to perform a complete lymph node dissection to locate that cancer cell.

Another reason that the sentinel lymph node biopsy is done in an open surgery operation (and not percutaneous biopsy) is that the surgeon has to avoid inadvertently cutting blood vessels or nerves during the procedure. Kelcz, U.S. Pat. No. 6,512,943, teaches the use of ultrasound imaging in conjunction with a gamma detection probe for percutaneous localization of the sentinel lymph node. Obtaining ultrasound images helps the surgeon from inadvertently cutting blood vessels or nerves, and helps the surgeon to insert a biopsy needle percutaneously to reach the sentinel lymph node or other lymph nodes. While Kelcz suggests that a percutaneous biopsy is adequate, practitioners have found that such a procedure is not effective in obtaining a reliable analysis of the sentinel node for cancer cells. Since the whole lymph node is still needed for the pathologist to assess if the lymph node contains any cancer cell, and it is nearly impossible to take out the lymph node intact or remove it in its entirety through the biopsy needle, this technique is of very limited value as this procedure can only determine that lymph node is positive if the partial sample happens to contain any cancerous cell. The procedure also lacks negative predictive value.

Examples of the several different designs for intraoperative radiation detection probes which might be used in the new procedures described herein include

- Scintillator-PMT systems, that use vacuum tube PMTs and scintillation crystals such as NaI(Tl),
- Scintillator-PIN diode systems that use PIN diodes as light detectors and then couple them to a scintillator with emissions around ~500 nm wavelength (such as CsI). The PIN diode has a gain of one (1) and therefore needs very low noise and high gain amplifiers,
- Cd—Te semiconductor detectors, that convert the energy from radiation directly to an electronic pulse
- Zn—Cd—Te semiconductor detectors that convert the energy from radiation directly to an electronic pulse.

A more recent development is a solid state or silicone photomultiplier (SSPM, or SiPM) developed by a team from the Moscow Engineering and Physics Institute (B Dolgoshein *Int. Conf. on New Developments in Photodetection* (Beaune, France) June 2002) together with Pulsar Enterprise in Moscow which promises a wide range of applications. The device is basically a large number of microphoton counters ($1000/mm^2$) which are located on a common silicon substrate and have a common output load. Each photon counter is a small (20-30 µm square) pixel with a depletion region of about 2 µm of less than 0.1 photoelectron. They are decoupled by polysilicon resistors and operate in a limited Geiger mode with a gain of approximately one million. This means that the SiPM is sensitive to a single photoelectron, with a very low noise level SiPM pixel operates digitally as a binary device, as a whole the SiPM is an analogue detector that can measure light intensity within a dynamic range of about $1000/mm^2$ and has excellent photon capability.

The pulse height spectrum of such a device is shown in FIG. 23. The photon detection efficiency of the SiPM is at about the same level as photomultiplier tubes (PMTs) in the blue region (20%), and is higher in the yellow-green region. The device has very good timing resolution (50 ps r.m.s. for one photoelectron) and shows very good temperature stability. It is also insensitive to magnetic fields. These characteristics mean that the SiPM can compete with other known photodetectors (e.g., PMT, APD, HPD, VLPC) and may prove useful for many applications, from very low light intensity detection in particle physics and astrophysics, through fast luminescence and fluorescence studies with low photon numbers in chemistry, biology and material science, to fast communication links. The main advantage of the SSPM is its small size (1×1 mm) and its low operating voltage of ~60 V. These characteristics render SSPM ideal for use in intraoperative and intra-luminal radiation detection probes and cameras such as shown in FIG. 24.

One currently proposed medical applications for SiPM is in a small field of view PET scanner that can work in high magnetic fields of an MRI scanner (Rubashov, I. B., U.S. Pat. No. 6,946,841).

SUMMARY

The present invention is directed to instruments and instrumental techniques for locating radio-labeled tissues which utilize a radiation detector operatively connected to an ultrasound probe for locating the exact position of radiation tagged tissue, particularly in sentinel lymph nodes or cancerous tumors followed by placement of a biopsy device. Also described are unique new interoperative radiation detection probes and cameras for use in these techniques which include structure for placement of a biopsy device or biopsy needle into the located node and procedures for removal of small portions of detected radiation emitting sentinel lymph nodes for evaluation in a pathology laboratory by measurement of expressed genes located in the removed tissue. The instruments and instrumental techniques also facilitate the subsequent delivery of materials to reverse the autoimmune response in the sentinel node once cancer cells are located therein.

BRIEF DESCRIPTION OF DRAWINGS

FIGS. 20a and 20b are cutaway side and end views, respectively, of a compact interoperative radiation detection probe containing an SiPM.

FIG. 21 is a schematic representation showing a cross sectional view of an embodiment of an endo-surgical radiation detector probe tip including a SiMP.

FIG. 22 is a schematic representation showing a SiMP mounted on a ring for mounting on a finger for use in locating tissue emitting radiation.

DETAILED DESCRIPTION

Certain molecular markers can be used as indicators of the status of the sentinel lymph node. For example, cytokine and chemokine gene expression in melanoma sentinel lymph nodes (SLN) varies with disease stage, i.e., whether cancer cells are present in the SNL or not. The pattern of inflammatory cytokines can be used to determine the presence of cancer in these lymph nodes. For example, the expression of molecular markers Interleukin-13 (IL-13), indoleamine 2,3-dioxygenase (IDO), interferon gamma (IFN), and interleukin-10 (IL-10) increases, and interleukin-11RA expression decreases, in tumor-position lymph nodes. Combinations of other molecular markers may determine the presence of cancer cells in other cancers such as breast cancer.

As shown in FIGS. 1-5, sentinel lymph nodes of stage III patients (tumor-bearing SNL's) show significantly higher gene expression of interleukin-13 (IL-13), leptin, lymphotoxin beta receptor (LTbR), and macrophage inflammatory protein-1b (MIP1b), and lower expression of macrophage maturation/activation gene (IL-11Ra) when compared with their levels in SLN's of patients that were Stage I or II (SLN that are free of cancer cells). These genes can therefore serve as new molecular surrogates for detecting occult SLN metastasis as they are reflective of the tumor-microenvironment and replace the need to slice and microscopically examine surgically removed sentinel nodes.

Figure 1:
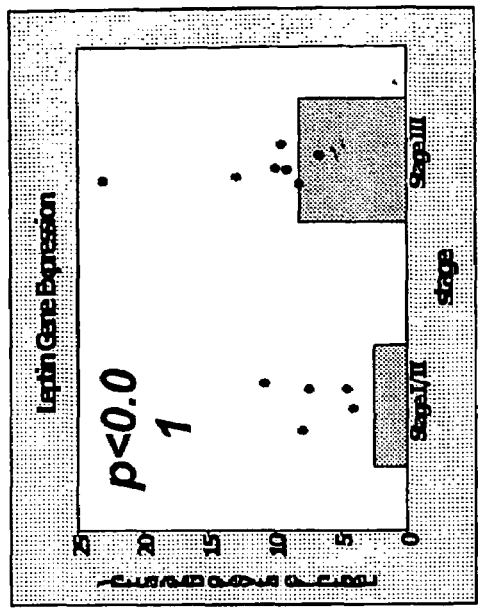
FIG. 1 is a graph showing expression of the IL-13 gene from sentinel lymph nodes of Stage I and Stage II patients compared with expression from Stage III patients.
Figure 3:
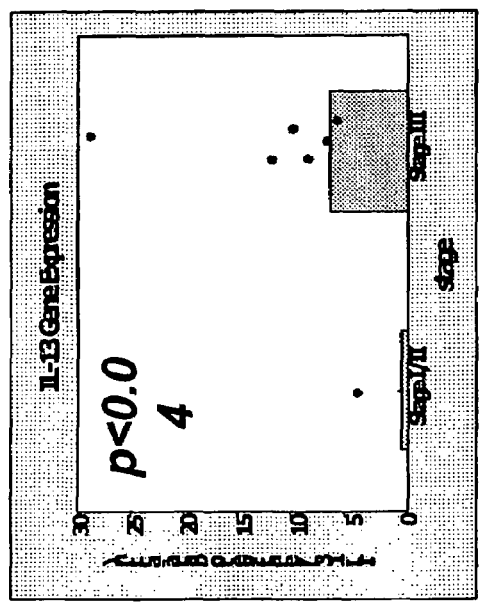
FIG. 3 is a graph showing expression of the LTbR gene from sentinel lymph nodes of Stage I and Stage II patients compared with expression from Stage III patients.
Figure 2:
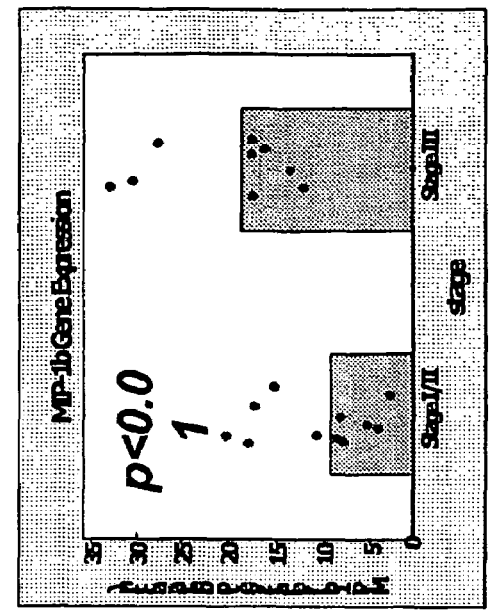
FIG. 2 is a graph showing expression of the leptin gene from sentinel lymph nodes of Stage I and Stage II patients compared with expression from Stage III patients.
Figure 4:
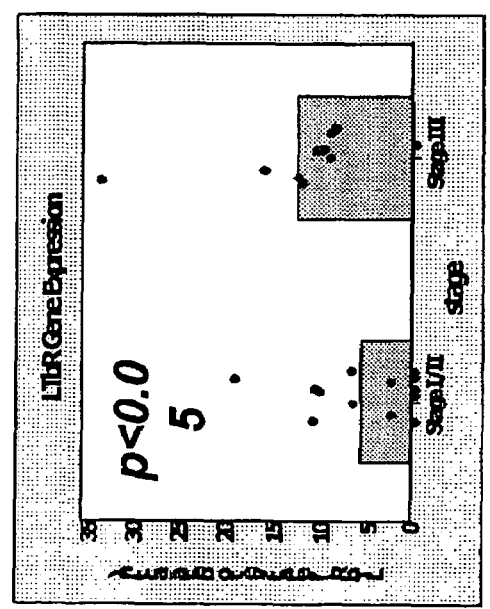
FIG. 4 is a graph showing expression of the MIP-1b gene from sentinel lymph nodes of Stage I and Stage II patients compared with expression from Stage III patients.
Figure 5:
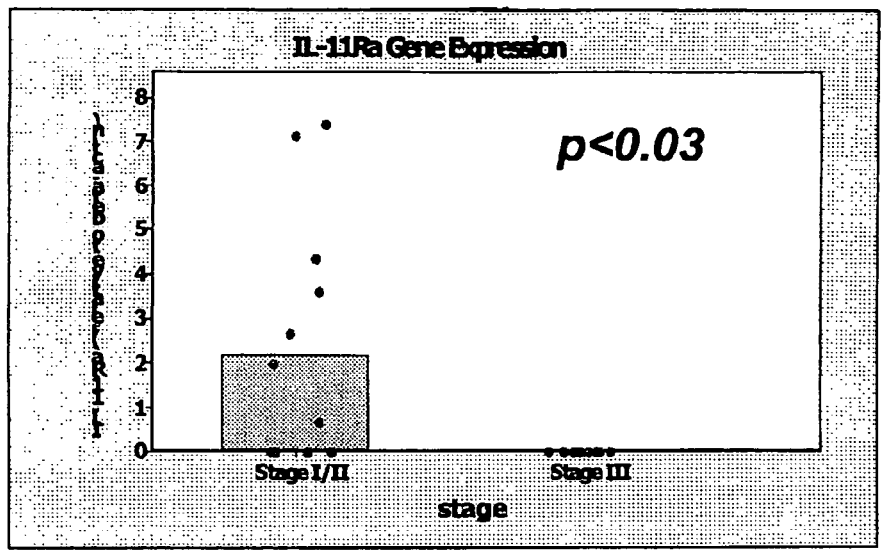
FIG. 5 is a graph showing the IL-11Ra gene expression from sentinel lymph nodes of Stage I and Stage II patients with the same gene expressed from Stage III patients.
Figure 6:
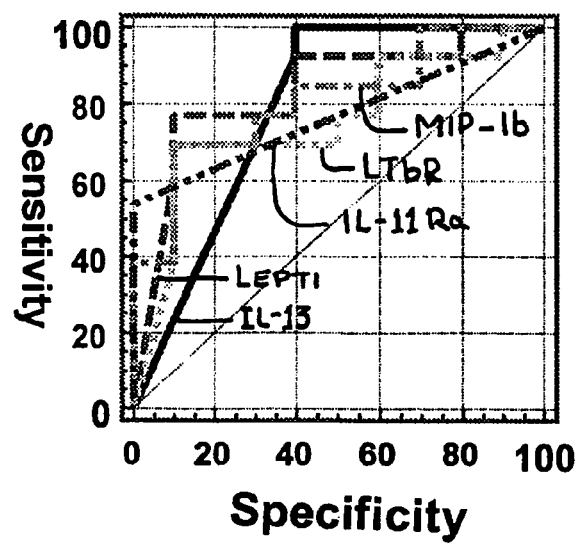
FIG. 6 is a graph of sensitivity versus specificity for detection of the five genes graphed in FIGS. 1-5.
Figure 7:
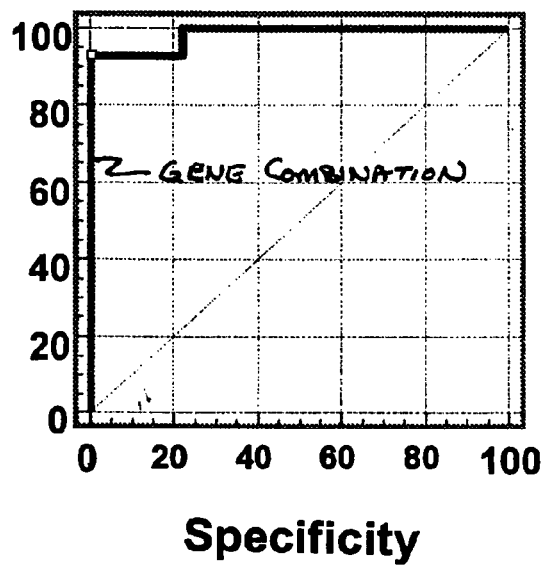
FIG. 7 shows the sensitivity versus specificity for detection of the five genes in combination.
Figure 8:
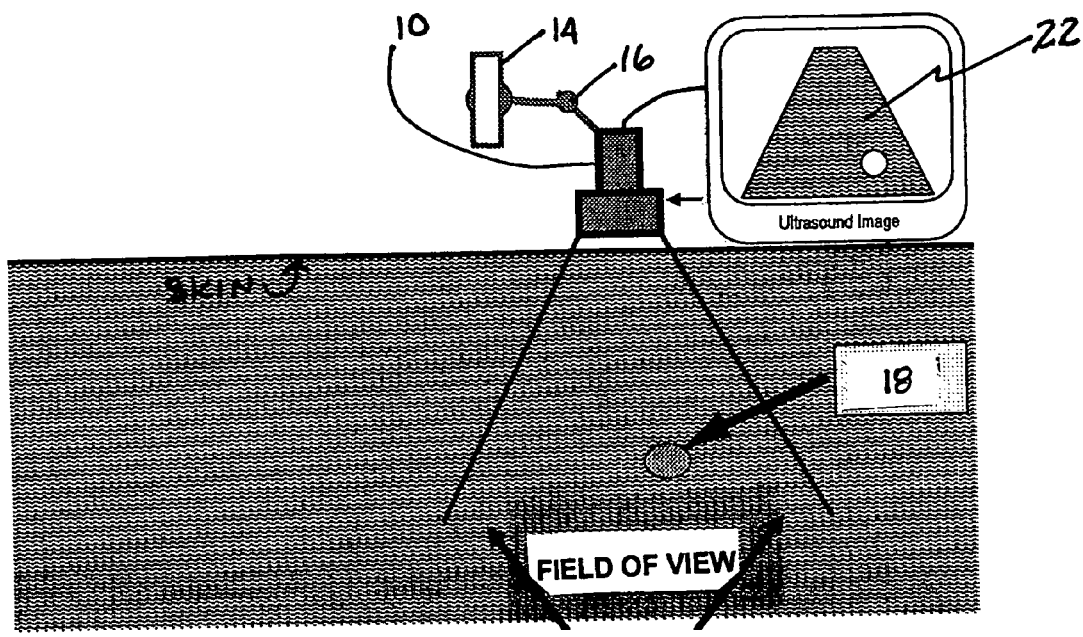
FIG. 8 is a schematic representation of the use of an ultrasound scanner to percutaneously target a sentinel node.
Figure 9:
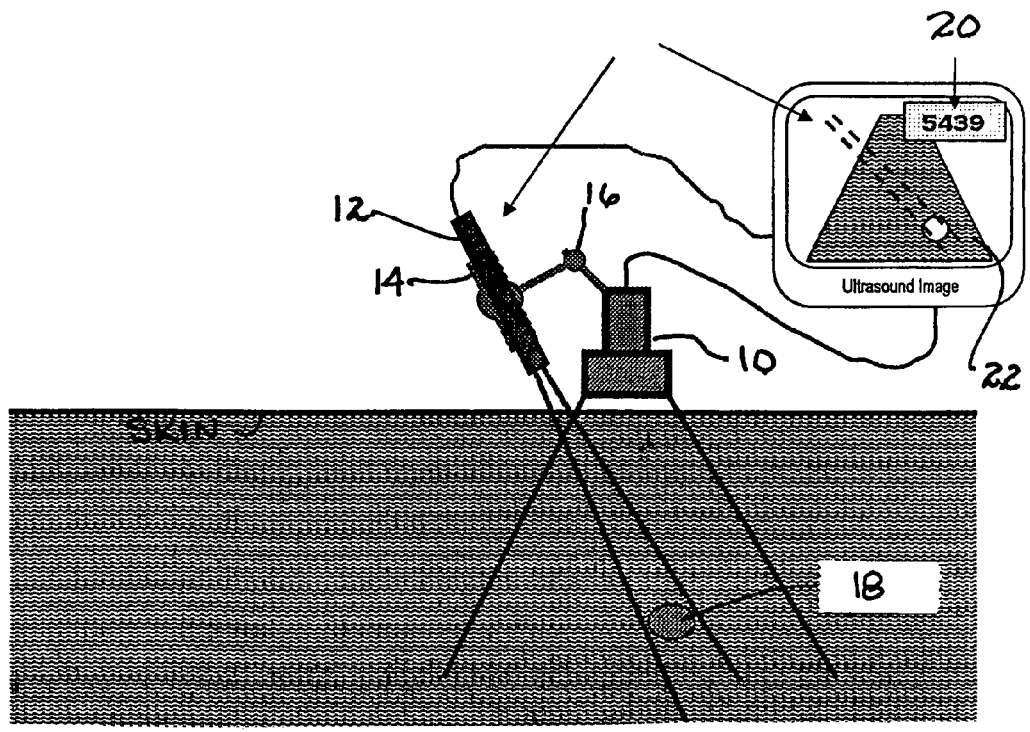
FIG. 9 is a schematic representation of the simultaneous use of an ultrasound probe and a radiation detector to percutaneously target a sentinel node.

As an example of a procedure that can be performed, RNA was extracted from freshly preserved SLNs of 13 AJCC stage I/II and 10 stage III (micromet<2 mm) melanoma patients. The RNA was then converted into biotin-16-dUTP labeled cDNA and amplified with 30 cycles of PCR. Expressed cytokine and chemokine genes were compared between the two groups by using a 96-gene cDNA microarray. Expression levels of individual genes were normalized to β-actin. Over- or under-expression was defined as a 2-fold increase or decrease, respectively. Statistical analysis was then performed with the Student's t-test and Receiver-Operator Characteristics (ROC) methods, demonstrating that the combination of all 5 markers is an excellent indicator of the stage of cancer (FIG. 7.)

Sentinel nodes from melanoma can be immunosuppressed by cytokines during the process of tumor metastasis. Accordingly, it has been found that conducting quantitative analysis of this melanoma induced cytokine-mediated immunosuppression in SLNs can be used to show the presence or absence of melanoma. Further, the sentinel node immunosuppression can be reversed by cytokine therapy; this reversal of immunosuppression in SLNs of Stage I or II melanomas may improve the cure rate of melanomas but can reduce the need for complete lymph node dissection. Other cancers, such as breast cancer, can also exhibit a certain pattern of SLN immunosuppression and may benefit in a similar fashion from cytokine therapy, gene therapy or RNA or DNA interference.

Several techniques for overcoming the shortcomings of prior techniques and for the use of percutaneous minimally invasive procedures for the determination of the status of SLNs, namely whether the SLN contains any tumor cells, without a surgical procedure and resection of the whole lymph node, are set below:

Method 1:

Using the technique described herein only a small piece of the sentinel lymph node is required in order to determine if it contains cancer cells. Instead of looking for the cancer cells, determining the level of a combination of molecular markers (such as those mentioned above) will provide information sufficient to establish the status of the lymph node and thereby the stage of the disease.

The sequence of the events, with reference to FIGS. 8-11, are:

The patient was injected with a radioactive substance, such as Tc-99m labeled sulfur colloid, in the area around the tumor.

1. After a time duration of about 1 to 48 hours, blue dye was injected around the tumor.

2. A few minutes later, an ultrasound scanner 10 with a gamma probe 12 mounted thereto through a holder 14 on a hinge arrangement 16 was used to localize the sentinel lymph node 18 percutaneously (FIG. 8 and FIG. 9) and the probe 12 was position to obtain the greatest radiation count 20, indicating that the location of the labeled sentinel node had been determined.

Figure 10:
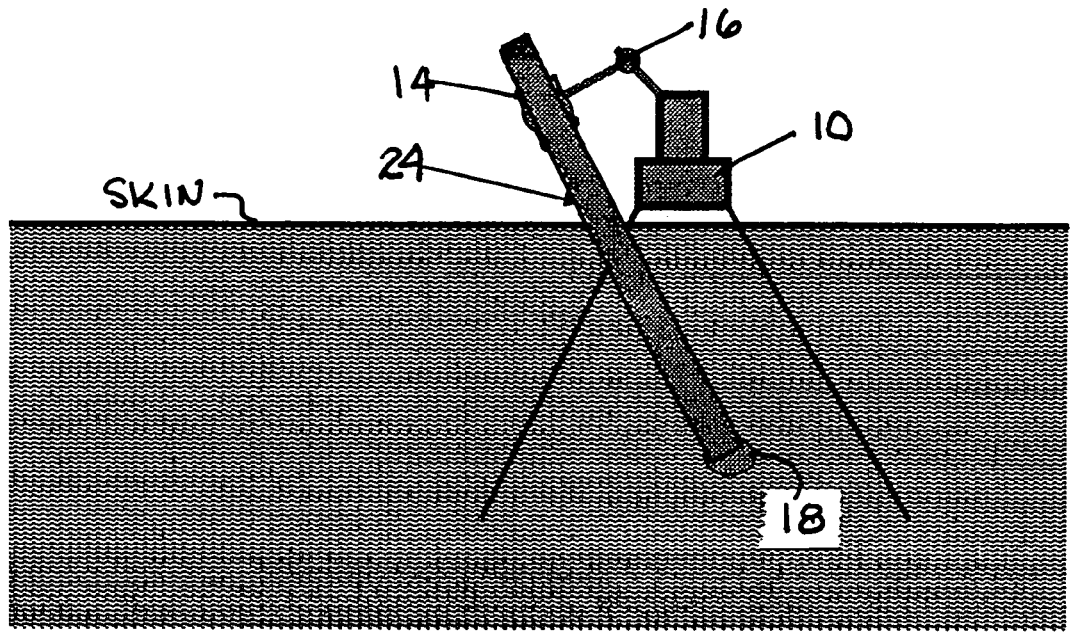
FIG. 10 is a schematic representation of the use an ultrasound scanner for placement of a biopsy apparatus into the lymph node along a path previously established by the assembly shown in FIG. 9.
Figure 11:
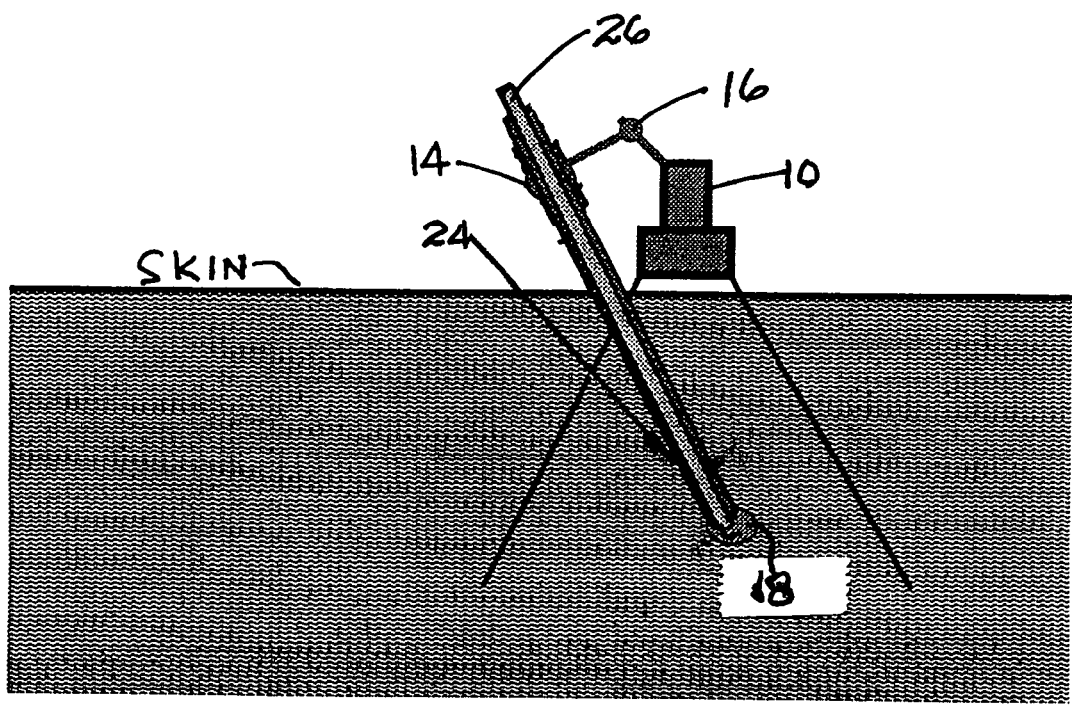
FIG. 11 is a schematic representation of a tissue collector or biopsy needle placed through the biopsy apparatus to collect a tissue sample from the node.

3. The position of the ultrasound scanner was held fixed, the probe was removed and, utilizing the established position of the holder 14 along with the ultrasound image 22 as a guide, a biopsy apparatus 24 was inserted into the lymph node 18 (FIG. 10). A tissue collector or biopsy needle 26 was then placed through the biopsy apparatus 24 and a tissue sample was collected from the node 18 (FIG. 11).

4. The presence of a particular molecular marker or array of markers, such as those mentioned above, and the quantity thereof, were determined on the biopsy sample using molecular biology methods such as quantitative RT-PCR (reverse transcriptase-polymerase chain reaction). This determined whether the lymph node was tumor-bearing or free of cancer cells.

5. Using the same node location technique, the same node or tumor was located and the lymph node or the tumor was injected with a therapeutic agent. Alternatively, a marker easily located by ultrasound techniques can be placed at the site of the sentinel lymph node so it can be readily located at a later time.

Figure 12:
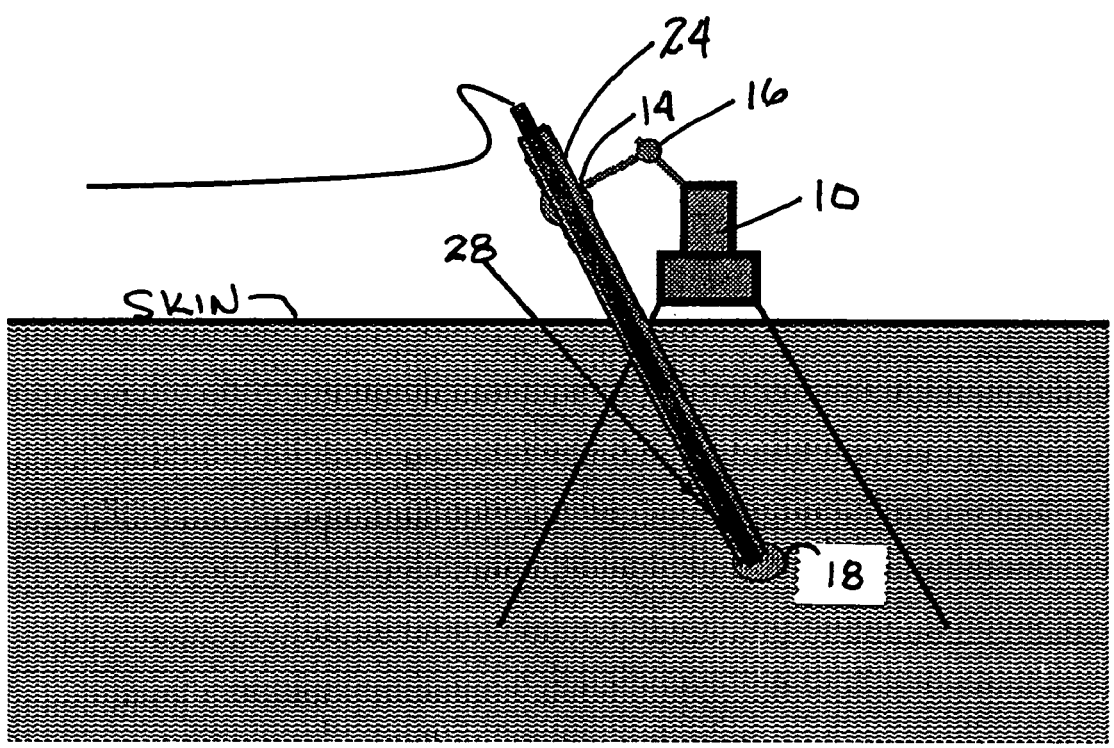
FIG. 12 is a schematic representation of the use of a long, narrow radiation detection probe, or intra-luminal probe placed through a biopsy apparatus in the holder on a hinged connection to the ultrasound scanner to detect the exact depth of the tagged sentinel node.

Method 2:

This method is a modification of the procedure set forth in Method 1 described above. In step 4 above, before inserting the tissue collector or biopsy needle into the node, a very narrow radiation detector probe 28, such as shown in FIG. 12, is inserted through the biopsy apparatus 24 to ascertain if the tip of that apparatus 24 is inside the radioactive sentinel node 18. The position of the biopsy apparatus is then adjusted such that maximum counts of the intra-luminal probe is achieved at the tip of the biopsy apparatus. If radioactivity is detected, the probe 28 is removed and the biopsy needle 26 is inserted and tissue collected followed by treatment.

Figure 13:
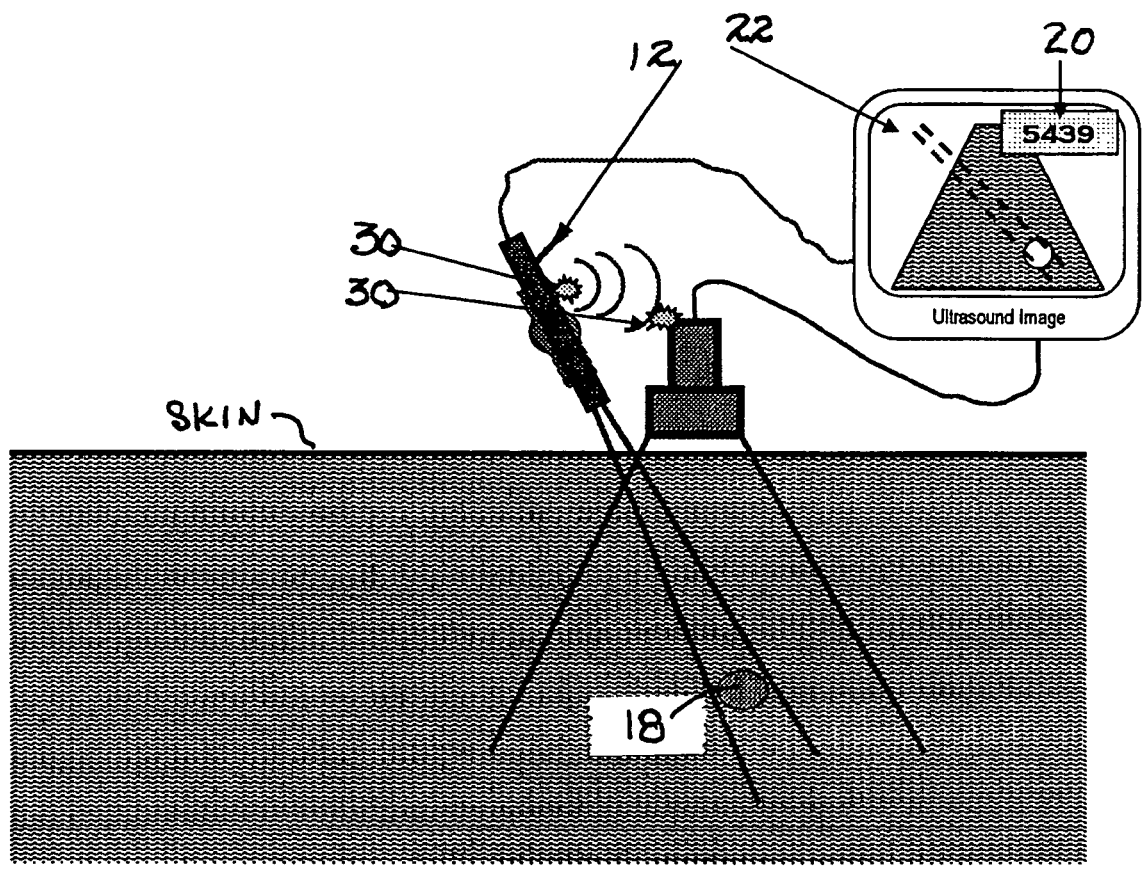
FIG. 13 is a schematic representation of a radiation probe and an ultrasound transducer electronically coupled by electromagnetic or acoustic position sensors mounted on each.

As a further alternative, as shown in FIG. 13, the mechanical hinge arrangement 16 between the probe and the ultrasound transducer can be replaced by a pair of electromagnetic, optical, or acoustic position sensors 30. This allows the position and direction (orientation) of the gamma probe 12 in relationship to the ultrasound transducer to be registered on a computer. A similar sensor 30 on the biopsy apparatus 24 can then be used to place it in the same position. Otherwise, all of the steps described above are followed.

Figure 14:
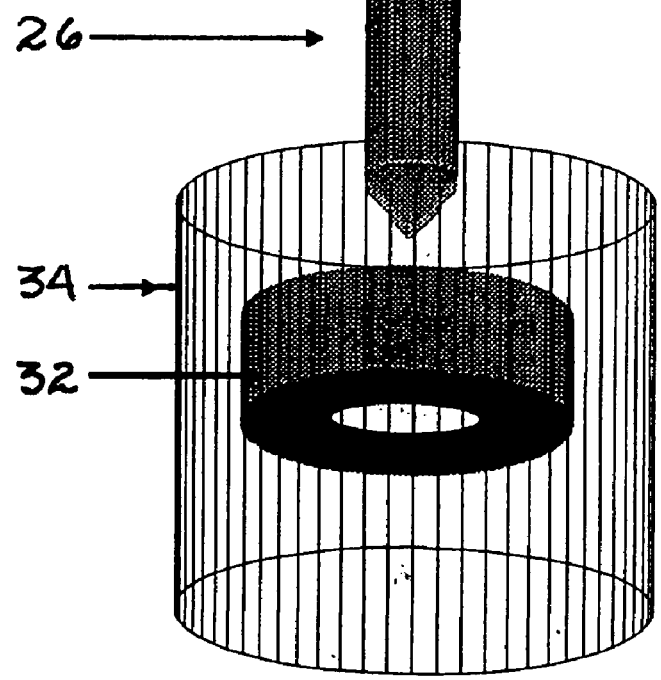
FIG. 14 is a schematic representation of a donut shaped radiation detector comprising a scintillating crystal sized to receive a biopsy needle or apparatus through its center.

Method 3:

This method incorporates a radiation detector with a hole there through along a central axis of the detector, or parallel to its axis. The radiation detector is surrounded by a heavy metal collimator (FIG. 14) which can be placed on the skin surface in the vicinity of the sentinel node. An opening or hole 36 in the detector 32 is sized to receive the biopsy apparatus 24 and/or biopsy needle 26. In one configuration this detector is made of a semiconductor material such as CdTe or ZnCdTe. Alternatively, the detector is a scintillating crystal that is optically connected to a photo-detector such as photomultiplier tube (PMT), solid-state photomultiplier (SSPM or SiPM), avalanche photodiode, or PIN photodiode.

Figure 15:
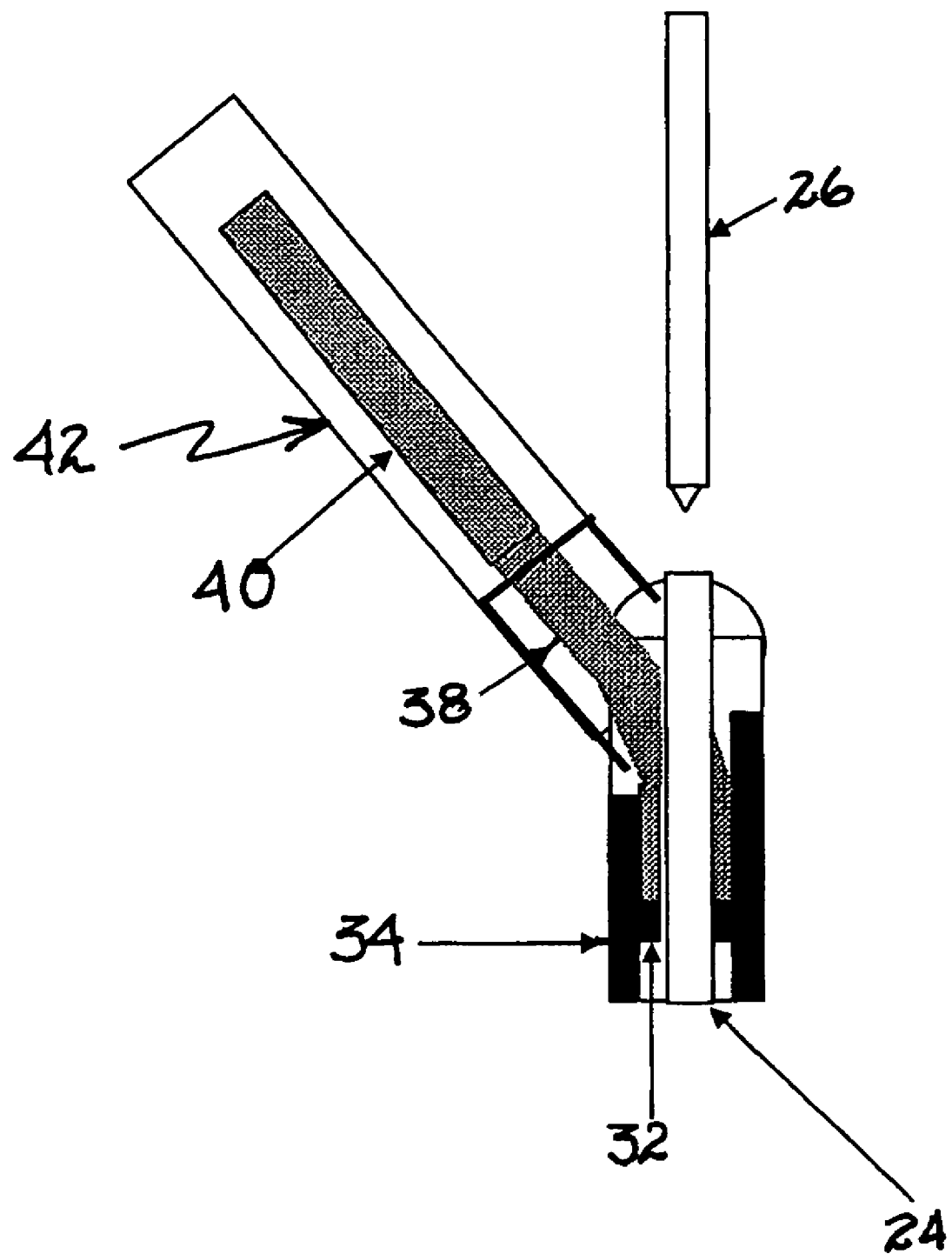
FIG. 15 is a schematic representation of the donut shaped detector of FIG. 14 with the scintillating crystal connected by an optical fiber bundle to a light detector.
Figure 16:
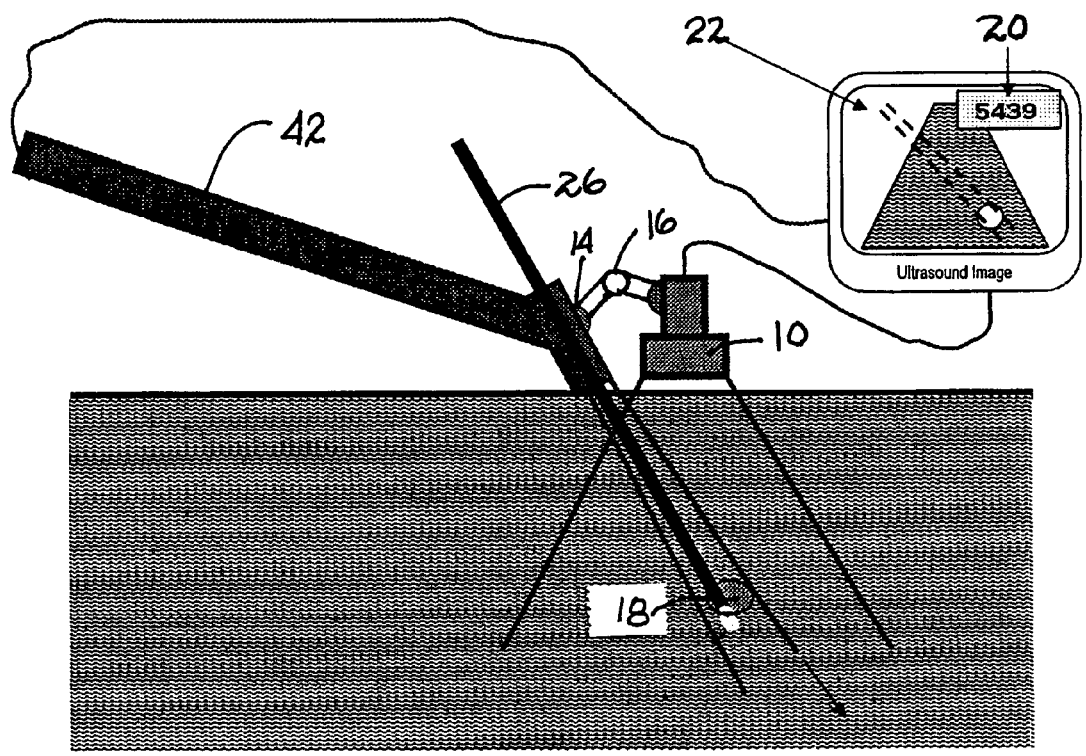
FIG. 16 is a schematic representation showing the radiation detector of FIG. 15 attached to an ultrasound detector by a hinged connector with a biopsy needle through the center of the radiation detector.

FIG. 15 shows radiation detector assembly (probe) 42 comprising a radiation detector with an axial hole (or a hole parallel to the axis) in it comprising BGO scintillating crystals radiation detector 32 within a tungsten collimator 34. The hole 36 in the detector provides a conduit for placement of a biopsy apparatus 24 and biopsy needle 26. The light generated by radiation in the scintillating crystal 32 is carried via an optical fiber bundle 38 of more than 1000 strands to a light detector 40 such as a PMT or SSPM or avalanche photodiode. FIG. 16 shows the radiation detector assembly (probe) 42 of FIG. 15 attached to a ultrasound detector 10 by a hinged connector 16. The probe 42 identifies the sentinel node 18 and the ultrasound transducer 10 images the anatomy of the tissue surrounding the sentinel node 18. This arrangement is operated in the same manner as set forth in Example 1.

Figure 17:
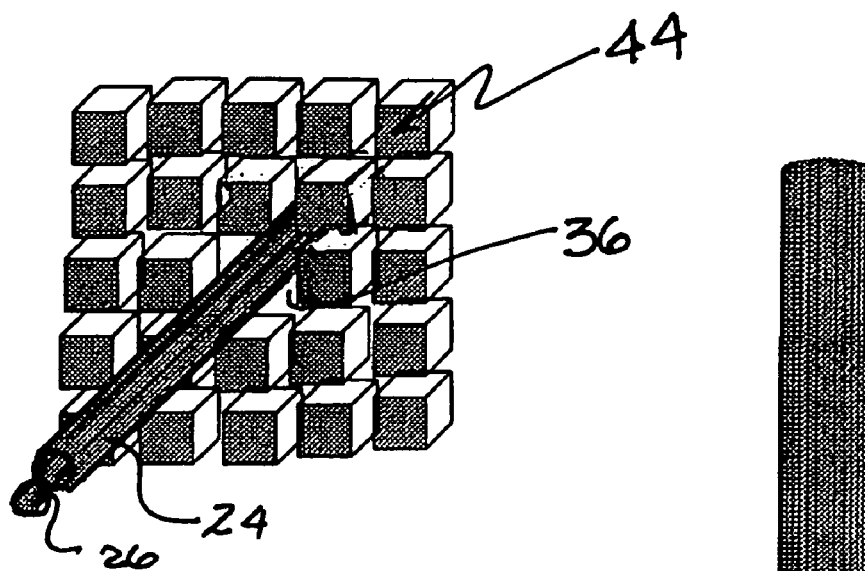
FIG. 17 is a schematic representation of an array of detectors that can act as a radiation detection camera, the array having a hole there through for placement of a biopsy needle.
Figure 18:
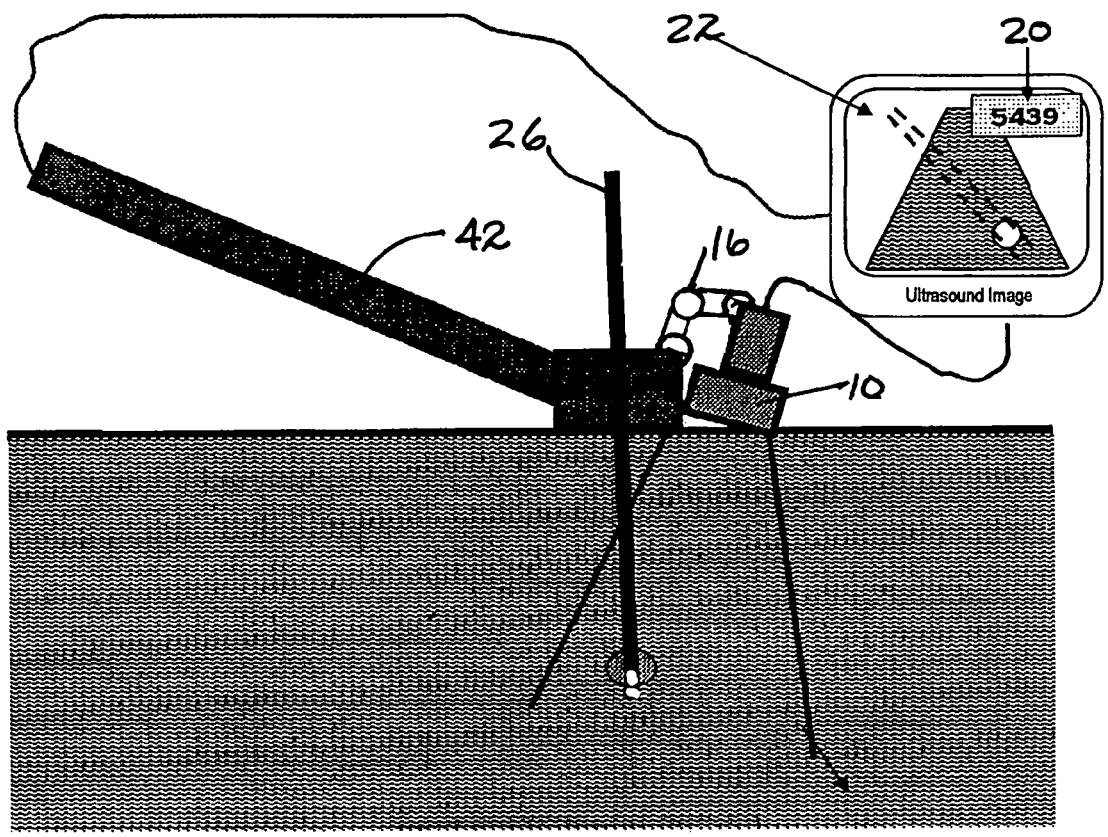
FIG. 18 is a schematic representation of an ultrasound detector connected to a radiation detector including the array assembly of FIG. 17 and a biopsy apparatus through the center of that array.
Figure 19:
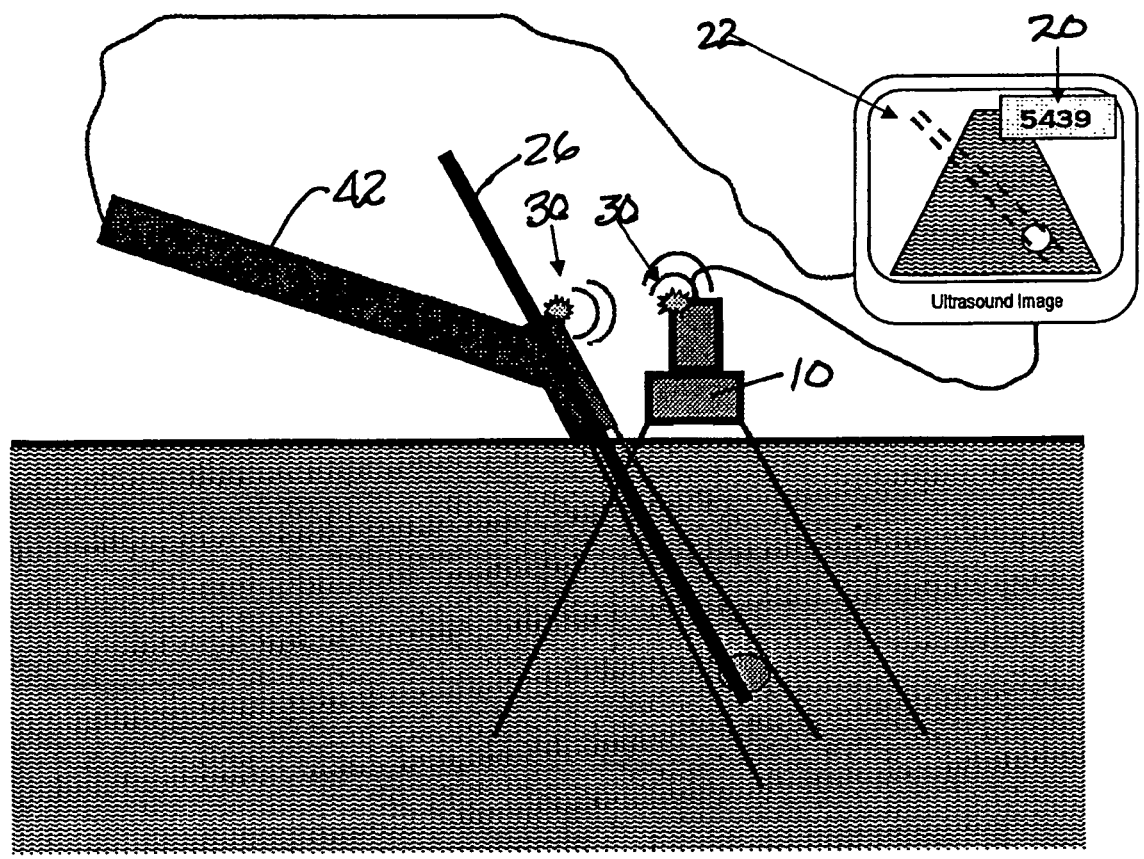
FIG. 19 is a schematic representation of the detector of FIG. 15 or the array of FIG. 17 along with an ultrasound detector and biopsy apparatus with electromagnetic or acoustic position sensors mounted on the array and detector to determine the relative positions of the detector or array.
Figure 23:
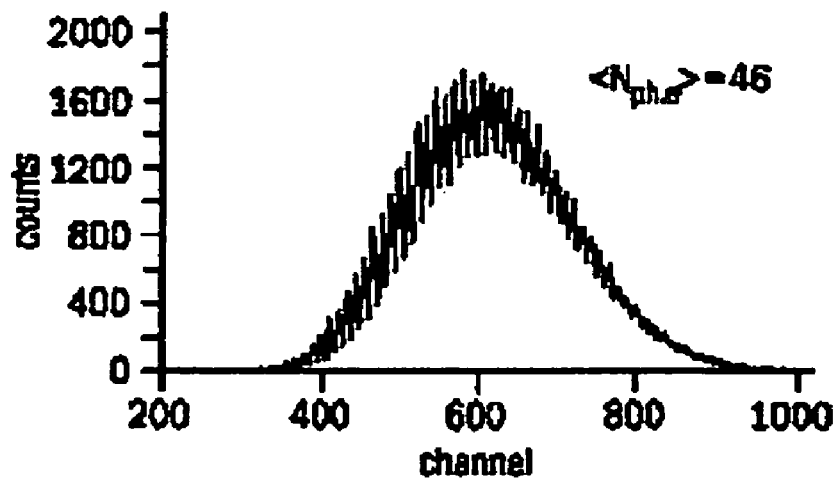
FIG. 23 is a graph showing the pulse height spectrum of a SiPM device.

FIG. 17 shows an array of detectors 44 used in place of the donut scintillator ring 32 to form an image of the radioactive distribution. A hole 36 is provided in the detector array 44 to accommodate a biopsy apparatus 24 and/or needle 26. The detector array 44 can comprise scintillators, or semdiconductor detectors. A parallel-hole collimator (not shown) may be put in front of the detector array 44 in order to form the image of the gamma ray emissions. This radiation detector can also be a beta ray camera, and photodetectors can be avalanche photodiode, SSPM or PMT. FIG. 18 shows a detector assembly 42 which includes the array 44 coupled to an ultrasound transducer 10 through a hinge connector 16 and FIG. 19 shows the same components, the relative positions of each being determined by wireless position sensors 30 mounted on each component.

Once a biopsy of the sentinel node 18 has been performed using one of the assemblies described, if treatment is appropriate the procedure described above can be used to once again locate this sentinel node or a second SLN 18. The localized sentinel lymph node 18 is then injected with therapeutic genetic materials, or cells that can reverse the immunosuppression caused by the cancer (such as melanoma cytokine-mediated immuno-suppression). As an example, a plasmid DNA vaccine (Tagawa et al. *Cancer;* 98, p144-54 (2003)), and/or cells engineered to secrete granulocyte-macrophage colony stimulating factor, and/or recombinant human granulocyte macrophage colony stimulating factor (rhGM-CSF) can be delivered. Injection of other compounds, or genetic materials or interfering nucleic acids and/or cells that boost the immune response of the sentinel node can also be beneficial. These may include recombinant GM-CSF-encoding virus as gene therapy, or RNA, DNA interference (RNAi). The direct injection of these materials into the sentinel node 18 is made possible by detection of the sentinel lymph node as described herein. An ultrasound or gamma probe detectable "clip" or particle can be placed on the SLN as a method to relocate the SLN for future evaluation or treatment with needle biopsy.

A limitation of current technology intra-operative probes is the size of the PMT (1 cm diameter and 5 cm long). Although CdTe, PIN diode, or ZCdTe all have compact sizes, they are all low gain, noise sensitive, and have low efficiencies for absorption of gamma rays. As a further alternative it is proposed that a SiPM or other solid state photomultiplier (SSPM) devices be used for detection of scintillation light of LSO, YLSO, and BGO scintillators that have high densities and therefore high absorption efficiencies for gamma rays. An interoperative probe 50 incorporating an SiPM is shown in FIGS. 20a and 20b. It comprises a scintillator 52 in front of a SiPM 54 with the circumference thereof in a surrounding collimator 56, preferably a gold collimator. A lead 58 extending from the SiPm 54 carries the signal to electronic display means such as shown on FIGS. 8, 9, 13, 16 and 17. Such an interoperative probe 50 can be used in any of the assemblies described above. Another embodiment, shown in FIG. 22, is a SiMP containing interoperative probe 50 mounted on a ring so it can be worn on a finger and used to locate the sentinel node emitting radiation.

In addition to use to locate sentinel nodes, as described above, beta or gamma probes constructed utilizing SSPM can be used for endovascular, endoscopy thorascopic and laparoscopy since they are small in size. FIG. 21 shows a cross sectional view of a new endo-surgical radiation detector probe tip 60, which includes within a single tubular sheath 62, the interoperative probe 50, a biopsy port 64, an irrigation channel 66 and a camera channel 68, a channel for placing a biopsy needle, an irrigation channel and a camera. If a plastic scintillator is coupled to the SiPM it becomes a detector that is preferentially sensitive to beta rays. A dual detector beta probe can be made similar to the one proposed by Daghighian et al. in *Journal of Medical Physics*, 1994, pp53. This dual detector probe is capable of simultaneously detecting the beta rays and gamma rays. A multidetector probe or radiation detection camera can be made for locating labeled tissue within the body containing isotopes emitting gamma or beta rays.

Figure 24:
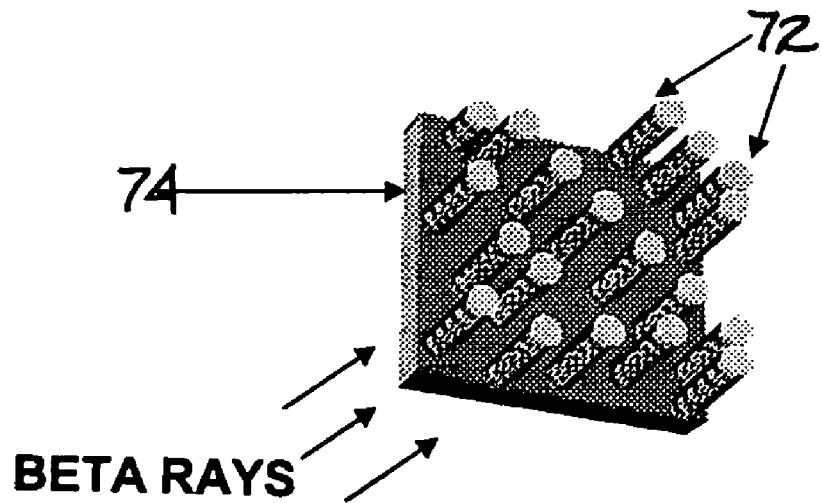
FIG. 24 is representation of a radiation detector camera constructed from SSPMs on a scintillator board.

A hand-held beta ray imaging camera for use in intra-operative detection of cancer can be made by coupling an array of SSPM's to a plate of plastic scintillator as shown in FIG. 24. An intraoperative gamma camera can be built in the same fashion by using SSPMs and a scintillator plate or individual pixels of scintillators (such as CsI). However, in such an instance, a parallel hole collimator of lead or tungsten should be put in front of the scintillator. Again the small size of the SSPM allows the shielding of this camera to be short and therefore result in a decrease in the weight of the camera. An intra-vascular beta probe constructed with SSPMs and scintillator(s) has the advantage of being able to work under relatively low voltages (60 V) and can be used for detection of inflammatory or vulnerable atherosclerosis plaques.

We claim:

1. A process for determining the stage of metastatic cancer in an individual diagnosed as having a malignant tumor comprising:
   a. injecting a radioactive substance into the individual in an area adjacent to the tumor, and allowing a period of time to elapse necessary for said radioactive substance to migrate to a sentinel lymph node, causing the sentinel node to become radioactive and emit radiation,
   b. placing an ultrasound scanner and a radiation probe comprising a gamma probe or radiation detecting camera on the skin surface in the region of the sentinel lymph node, the ultrasound scanner and a radiation probe being operatively connected so that the relative position and orientation to each other and to the sentinel lymph node is mechanically or electronically fixed or determined, with the sentinel lymph node being in the field of view of the ultrasound scanner and the radiation probe aimed at the radiation emitting sentinel lymph node, the direction or orientation of the radiation probe being adjusted to obtain the maximum possible radiation count from a targeted sentinel lymph node, the direction and orientation being shown on an image display of the ultrasound scanner in real time,
   c. while holding the ultrasound scanner fixed, removing the radiation probe and placing a biopsy needle in the same orientation as established for the radiation probe in step b above and advancing a distal tip thereof through the skin and into the targeted sentinel lymph node, the placement of the biopsy needle being displayed on the ultrasound scanner in real time, and
   d. collecting a tissue sample comprising a portion of the targeted sentinel lymph node for subsequent analysis by quantitative RT-PCR to determine the presence or absence of particular molecular tumor makers within the portion removed from the sentinel lymph node.

2. The process of claim 1 wherein a biopsy apparatus is placed percutaneously in the same orientation as the radiation probe, the biopsy needle being placed along a lumen in the biopsy apparatus.

3. The process of claim 2 further including the step of placing a second radiation probe through the biopsy apparatus prior to insertion of the biopsy needle to verify the location of the sentinel node.

4. The process of claim 1 wherein the ultrasound scanner and a radiation probe are operatively connected by a hinge arrangement mounted there between, the radiation probe being removably held in a holder attached to the hinged arrangement, a biopsy apparatus or the biopsy needle placed in the holder following removal of the radiation probe utilizing the established position of the holder as a guide for advancing the distal tip of biopsy apparatus or biopsy needle percutaneously to the location of the sentinel lymph node.

5. The process of claim 1 wherein the ultrasound scanner and a radiation probe are operatively connected by a first position sensor mounted on the ultrasound scanner and a second position sensor mounted on the radiation probe, a biopsy apparatus or the biopsy needle having a third sensor mounted thereon for orienting the biopsy apparatus or biopsy needle, after removal of the radiation probe, in the same orientation previously occupied by the radiation probe.

6. The process of claim 1 wherein the quantitative RT-PCR analysis is used to determine the presence of one or more of expressed molecular markers selected from the group consisting of IL-13, leptin, LTbR, MIP-1b, IL-11Ra, IDO, IFN gamma and IL-10, the quantity of one or more thereof indicative of infiltration of cancer cells into the sentinel lymph node.

7. The process of claim 1 further including the step of delivering to the targeted sentinel lymph node a therapeutic agent to prevent or retard the spreading of cancer cells through the lymphatic channels.

8. The process of claim 7 wherein the therapeutic agent comprises a compound that provides cytokine therapy, plasmid DNA vaccine, and/or cells engineered to secrete granulocyte-macrophage colony stimulating factor, and/or recombinant human granulocyte macrophage colony stimulating factor (rhGM-CSF), genetic materials and/or cells that boost the immune response of the sentinel lymph node and other nodes adjacent thereto comprising gene therapy, recombinant GM-CSF-encoding virus as gene therapy, or RNA or DNA interference.

9. The process of claim 1 further including placement of an ultrasound-detectable marker in or adjacent the sentinel lymph node contemporaneous with removal of the tissue sample for future use in detecting the prior location of a radiation emitting sentinel lymph node.

10. A process for determining the stage of cancer in an individual diagnosed as having a malignant tumor comprising:
   a. injecting a radioactive substance into the individual in an area adjacent the tumor, and allowing a period of time to elapse necessary for said radiation to migrate to a sentinel lymph node, causing the sentinel lymph nodes to become a radioactive labeled node,
   b. placing an ultrasound scanner and a radiation detector comprising a gamma probe or radiation detecting camera on the skin surface in the region of the sentinel lymph node, the ultrasound scanner and a radiation detector being operatively connected so that the relative position and orientation to each other and to a targeted sentinel lymph node is mechanically or electronically fixed or determined, with the targeted sentinel lymph node being in the field of view of the ultrasound scanner and the radiation detector aimed at the targeted radioactive sentinel lymph node, the direction or orientation of the radiation detector being adjusted to obtain a maximum possible radiation count from the targeted sentinel lymph node, indicating that the radioactive labeled node had been targeted, the radiation detector having a channel parallel to its axis of orientation, the channel sized to receive a biopsy device or biopsy needle,
   c. while holding the ultrasound scanner and radiation detector fixed, placing a biopsy apparatus or biopsy needle or both a biopsy apparatus and a biopsy needle through the channel with a distal tip thereon oriented toward the radioactive labeled node and advancing the distal tip thereof through the skin and into the radioactive labeled node, the location of the biopsy needle being displayed on the ultrasound scan in real time, and
   d. collecting a tissue sample from a portion of the radioactive labeled node for subsequent quantitative RT-PCR analysis to determine the existence of cancer cells in the tissue sample of the radioactive labeled node.

11. The process of claim 10 wherein a biopsy apparatus is placed through the axial channel and percutaneously in the same orientation as the radiation probe, the biopsy needle being placed along a lumen in the biopsy apparatus.

12. The process of claim 10 wherein the ultrasound scanner and radiation detector are operatively connected by a hinge arrangement mounted there between, the hinged arrangement holding the relative positions of the ultrasound scanner and radiation detector fixed while the distal tip of the biopsy apparatus or the biopsy needle is advanced percutaneously to the location of the radioactive labeled node.

13. The process of claim 10 wherein the ultrasound scanner and the radiation detector are operatively connected by a first position sensor mounted on the ultrasound scanner and a second position sensor mounted on the radiation detector, the relative positions of said first and second position sensors used to maintain a fixed orientation previously established there between during collection of the tissue sample from the radioactive labeled node.

14. The process of claim 10 further including the step of placing a radiation probe through the biopsy apparatus prior to insertion of the biopsy needle to verify the location of the radioactive labeled nodes.

15. The process of claim 10 wherein the quantitative RT-PCR analysis is used to determine the presence of one or more of expressed molecular markers selected from the group consisting of IL-13, leptin, LTbR, MIP-1b, IL-11Ra, IDO, IFN gamma and IL-10 the quantity of one or more thereof indicative of infiltration of cancer cells into the sentinel lymph node.

16. The process of claim 10 further including placement of an ultrasound-detectable marker in or adjacent the sentinel lymph node contemporaneous with removal of the tissue sample for future use in detecting the prior location of the radioactive labeled node.

17. The process of claim 10 wherein the radiation detector is a scintillator array with a hole in the center of the array for placement of a biopsy needle therethrough.

18. The process of claim 17 wherein the radiation detector is a donut-shaped detector.

19. The process of claim 10 wherein the radiation detector is an array of SiPM detectors coupled to at least one scintillator piece forming a gamma camera and having at least one channel therein for placement of the biopsy apparatus therethrough.

20. The process of claim 10 further including the step of delivering to the sentinel lymph node a therapeutic agent to prevent or retard the spreading of cancer cells through the lymphatic channels.

21. The process of claim 20 wherein the therapeutic agent comprises a compound that provides cytokine therapy, plasmid DNA vaccine, and/or cells engineered to secrete granulocyte-macrophage colony stimulating factor, and/or recombinant human granulocyte macrophage colony stimulating factor (rhGM-CSF), genetic materials and/or cells that boost the immune response of the sentinel lymph node and other nodes adjacent thereto comprising gene therapy, recombinant GM-CSF-encoding virus as gene therapy, or RNA or DNA interference.

* * * * *